(12) United States Patent
Cherpeck et al.

(10) Patent No.: US 8,003,583 B2
(45) Date of Patent: *Aug. 23, 2011

(54) BENZO[B]PERHYDROHETEROCYCLIC ARYLAMINES AND LUBRICATING OIL COMPOSITIONS

(75) Inventors: Richard E. Cherpeck, Cotati, CA (US); Carrie Y. Chan, Daly City, CA (US)

(73) Assignee: Chevron Oronite Company LLC, San Ramon, CA (US)

( * ) Notice: Subject to any disclaimer, the term of this patent is extended or adjusted under 35 U.S.C. 154(b) by 480 days.

This patent is subject to a terminal disclaimer.

(21) Appl. No.: 11/316,258

(22) Filed: Dec. 21, 2005

(65) Prior Publication Data

US 2007/0142246 A1 Jun. 21, 2007

(51) Int. Cl.
*C10M 135/36* (2006.01)
*C10M 135/32* (2006.01)
*C07D 263/60* (2006.01)
*C07D 277/62* (2006.01)

(52) U.S. Cl. ........ 508/269; 508/270; 508/271; 548/152; 548/217; 548/307.1

(58) Field of Classification Search ........... 508/261, 508/269, 270, 271; 546/165; 548/152, 217, 548/307.1
See application file for complete search history.

(56) References Cited

U.S. PATENT DOCUMENTS

| | | | |
|---|---|---|---|
| 1,896,461 A * | 2/1933 | Muth | ............. 546/101 |
| 2,342,135 A | 2/1944 | Gibbs | |
| 2,419,334 A | 4/1947 | Conn et al. | |
| 2,718,501 A | 9/1955 | Harle | |
| 2,794,020 A | 5/1957 | Harris et al. | |
| 2,943,112 A | 6/1960 | Popoff et al. | |
| 2,958,663 A | 11/1960 | Westcott et al. | |
| 2,998,468 A | 8/1961 | Wilde | |
| 3,345,992 A | 10/1967 | Lederman et al. | |
| 3,362,929 A * | 1/1968 | Kehe | ............. 524/87 |
| 3,362,930 A | 1/1968 | Kehe | |
| 3,452,056 A | 6/1969 | Sundholm | |
| 3,480,635 A | 11/1969 | Altwicker | |
| 3,505,225 A | 4/1970 | Wheeler | |
| 3,533,992 A | 10/1970 | Sundholm | |
| 3,655,559 A | 4/1972 | Holt | |
| 3,660,290 A | 5/1972 | Schlobohm | |
| 3,910,918 A | 10/1975 | Monroy | |
| 3,944,492 A | 3/1976 | Wheeler | |
| 4,069,195 A | 1/1978 | Layer et al. | |
| 4,089,792 A | 5/1978 | Lowe | |
| 4,402,859 A * | 9/1983 | Tamura et al. | ........ 252/401 |
| 4,692,258 A | 9/1987 | Rasberger et al. | |
| 4,965,006 A | 10/1990 | Meier et al. | |
| 5,198,134 A | 3/1993 | Steinberg et al. | |
| 5,232,614 A | 8/1993 | Colclough et al. | |
| 5,310,491 A | 5/1994 | Downs et al. | |
| 5,420,354 A | 5/1995 | Malz et al. | |
| 5,451,702 A | 9/1995 | Stern et al. | |
| 5,595,963 A | 1/1997 | Puckace et al. | |
| 5,834,544 A | 11/1998 | Lin et al. | |
| 6,121,209 A | 9/2000 | Watts et al. | |
| 6,174,842 B1 | 1/2001 | Gatto et al. | |
| 6,315,925 B1 | 11/2001 | Aebli et al. | |
| 6,426,324 B1 | 7/2002 | Lai et al. | |
| 6,806,241 B2 | 10/2004 | Karol et al. | |
| 7,501,368 B2 * | 3/2009 | Flink et al. | ........ 501/64 |
| 2003/0030033 A1 * | 2/2003 | Duyck et al. | ........ 252/380 |
| 2005/0188480 A1 * | 9/2005 | Lim et al. | ........ 8/405 |
| 2007/0142246 A1 * | 6/2007 | Cherpeck et al. | ........ 508/269 |

FOREIGN PATENT DOCUMENTS

GB 1106949 3/1968

OTHER PUBLICATIONS

McQueen, J.S. et al., Friction and wear of tribofilms formed by zinc dialkyl dithiophosphate antiwear additive in low viscosity engine oils, Elsevier Science Ltd., Tribology International 38, (2005), pp. 289-297.
Ingold, K.U., Inhibition of the Autoxidation of Organic Substances in the Liquid Phase, Division of Applied Chemistry, National Research Council Publication No. 6537, American Chemical Society, Chemical Reviews, vol. 61, (1961), pp. 563-589.
Nishiyama, Tomohiro et al., Antioxidant activity of the fused heterocyclic compounds, 1,2,3,4-tetrahydroquinolines, and related compounds—effect of *ortho*-substituents, Elsevier Science Ltd., Polymer Degradation and Stability 79, (2003), pp. 225-230.
Dorey, Gilbert et al., New Quinolinic Derivatives as Centrally Active Antioxidants, Elsevier Science Ltd., Bioorganic & Medicinal Chemistry Letters 10, (2000), pp. 935-939.
Denisov, Evgeniy T. et al., Mechanisms of Action and Reactivities of the Free Radicals of inhibitors, American Chemical Society, Chemical Reviews, vol. 87, No. 6 (1987), pp. 1313-1357.
Nishiyama, Tomihiro et al., Antioxidant activity of aromatic cyclic amine derivatives, Elsevier Science Ltd., Polymer Degradation and Stability 75, (2002), pp. 549-554.
Chatel et al.: "Synthesis of new N-alkl- and N-acyldioxinophenothiazine and acridinole derivatives" Heterocycles, vol. 53, No. 11, 2000, pp. 2535-2552, XP008077187 UMR 6009, Laboratoire de Valorisation de la Chimie Fine, France.

* cited by examiner

*Primary Examiner* — Yong Chu
(74) *Attorney, Agent, or Firm* — Joseph P. Foley

(57) ABSTRACT

Benzo[b]perhydroheterocyclic arylamine compounds have shown to be particularly useful as stabilizers. The compounds may serve as antioxidants, antiozoants, heat stabilizers and ultraviolet light stabilizers and such compounds are oil soluble, thus particularly suited for use as an antioxidant in a lubricating oil composition.

7 Claims, No Drawings

BENZO[B]PERHYDROHETEROCYCLIC ARYLAMINES AND LUBRICATING OIL COMPOSITIONS

FIELD OF THE INVENTION

Benzo[b]perhydroheterocyclic arylamines compounds have demonstrated utility in mitigating oxidation in functional fluids. Accordingly, the present invention is directed to substituted and unsubstituted Benzo[b]perhydroheterocyclic arylamines compounds and lubricating compositions containing such.

BACKGROUND OF THE INVENTION

Diarylamine antioxidants are known and have been widely used to improve the thermal-oxidative stability and/or light induced degradation in numerous products used in engineering; for example, they can improve the performance properties in lubricants, hydraulic fluids, metal working fluids, fuels or polymers, just to name a few.

Commonly, these diarylamines have been alkylated, see for example, U.S. Pat. No. 2,943,112 which discloses an improved process for alkylating diphenylamine and U.S. Pat. No. 3,655,559 which discloses alkylated diphenylamines as stabilizers. Alkaryl substituted diphenylamines and phenyl-napthylamines (such as α-methylstyryl-diphenylamine) are disclosed for example in U.S. Pat. Nos. 3,533,992; 3,452,056 and 3,660,290. Substituted paraphenylene diamines have also been disclosed as antioxidants for lubricants in which iron-catalyzed oxidation reaction can occur, see U.S. Pat. No. 5,232,614.

Additionally, alkyl substituted 1,2-dihydroquinoline and polymers thereof, have been employed as antioxidants, see U.S. Pat. Nos. 3,910,918. While, U.S. Pat. No. 5,310,491 discloses the reaction product of an alkyl substituted 1,2-dihydroquinoline with a diarylamine. Tetrahydroquinones and substituted tetrahydroquinones have also have also been disclosed as antioxidants, see for example U.S. Pat. Nos. 2,794,020; 3,362,929; 4,692,258 and 4,965,006. Likewise decahydroquinolines and substituted decahydroquinolines have been employed as antioxidants, see U.S. Pat. Nos. 2,998,468 and 4,069,195.

In order to satisfy the more severe operating conditions and new applications which require improved oxidation inhibition, continued development of new compounds to mitigate oxidation is of paramount interest. The compounds of the present invention demonstrate superior performance in an organic substrate and thus may serve the continued need.

SUMMARY OF THE INVENTION

The present invention is directed in part to compounds which may serve as antioxidants, antiozoants, heat stabilizers and ultraviolet light stabilizers and such compounds are oil soluble, thus particularly suited for use as an antioxidant in a lubricating oil composition. Accordingly, the present invention discloses a compound according to formula I:

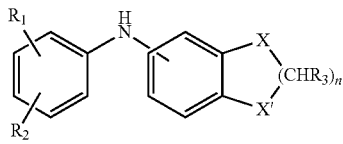

Formula I wherein
$R_1$ and $R_2$ are each independently selected from the group consisting of hydrogen, alkyl from 1 to 20 carbon atoms, —OR, —SR and —NRR', where R and R' are independently hydrogen or alkyl from 1 to 6 carbon atoms, or $R_1$ and $R_2$ when adjacent to each other together form a 5 to 6 membered alicyclic or aromatic ring which may be optionally substituted with 1 or 2 alkyl groups each having from 1 to 20 carbon atoms;
each $R_3$ is hydrogen or alkyl from 1 to 6 carbon atoms,
X and X' are independently selected from —$CHR_4$—, oxygen, sulfur or $NR_5$, wherein $R_4$ and $R_5$ are independently hydrogen or alkyl from 1 to 6 carbon atoms, with the proviso that at least one of X or X' is a heteroatom positioned ortho or para to the bridging nitrogen atom, and when X or X' are nitrogen then $R_1$ or $R_2$ is not hydroxyl; and further provided that when one of X or X' is —$CHR_4$— then the other may not be oxygen; and n is an integer from 1 to 2.

The benzo[b]perhydroheterocycle can contain one or two heteroatoms and preferably contains at least one nitrogen or oxygen atom, with nitrogen being particularly preferred, thus in this aspect at least one X or X' is oxygen of $NR_5$, with —NH— being particularly preferred. The single nitrogen benzo[b]perhydroheterocycle can be characterized as having being unsubstituted on the heterocyclic ring but, optionally substituted on the aryl ring, thus $R_1$ and $R_2$ are each independently selected from the group consisting of hydrogen, alkyl from 1 to 20 carbon atoms, —OR, —SR and —NRR', where R and R' are independently hydrogen or alkyl from 1 to 6 carbon atoms, or $R_1$ and $R_2$ when adjacent to each other together form a 5 to 6 membered alicyclic or aromatic ring which may be optionally substituted with 1 or 2 alkyl groups each having from 1 to 20 carbon atoms, and more particularly wherein $R_1$ and $R_2$ are each independently selected from the group consisting of hydrogen and alkyl from 1 to 20 carbon atoms.

In yet another aspect, X and X' are independently selected from oxygen, sulfur or $NR_5$, wherein $R_5$ is hydrogen or alkyl from 1 to 6 carbon atoms. Thus, both X and X' can be oxygen or for example, nitrogen.

In the compounds of formula I, $R_1$ and $R_2$ together with the atoms between them, can form alicyclic or aromatic ring. Thus, one aspect of the compound is directed to when $R_1$ and $R_2$ are adjacent to each other and together form a 5 to 6 membered aromatic ring which may be optionally substituted with 1 or 2 alkyl groups each having from 1 to 20 carbon atoms. Other aspects are characterized for example, wherein $R_1$ is hydrogen and $R_2$ is selected from the group consisting of alkyl from 1 to 20 carbon atoms, —OR, —SR and —NRR', where R and R' are independently hydrogen or alkyl from 1 to 6 carbon atoms, with the tertiary amines being preferred.

Another aspect of this invention is directed to lubricating compositions comprising a major amount of an oil of lubricating viscosity and a compound of formula I as described herein above.

DETAILED DESCRIPTION OF THE INVENTION

Inhibition of free radical-mediated oxidation is one of the most important reactions in organic substrates and is commonly used in rubbers, polymers and lubrication oils; namely, since these chemical products may undergo oxidative damage by the autoxidation process. Hydrocarbon oxidation is a three step process which comprises: initiation, propagation and termination. Oxidative degradation and the reaction mechanisms are dependent upon the specific hydrocarbons, temperatures, operating conditions, catalysts such as metals, etc., which more detail can be found in Chapter 4 of Mortier R. M. et al., 1992, "Chemistry and Technology of Lubricants Initiation", VCH Publishers, Inc.; incorporated herein by reference in its entirety. Initiation involves the reaction of oxygen or nitrogen oxides ($NO_x$) on a hydrocarbon molecule. Typically, initiation starts by the abstraction of hydrocarbon proton. This may result in the formation of hydrogen peroxide (ROOH) and radicals such as alkyl radicals (R.) and peroxy radicals (ROO.). During the propagation stage, hydroperoxides may decompose, either on their own or in the presence of catalysts such as metal ions, to alkoxy radicals (RO.) and peroxy radicals. These radicals can react with the hydrocarbons to form a variety of additional radicals and reactive oxygen containing compounds such as alcohols, aldehydes, ketones and carboxylic acids; which again can further polymerize or continue chain propagation. Termination results from the self termination of radicals or by reacting with oxidation inhibitors.

The uncatalyzed oxidation of hydrocarbons at temperatures of up to about 120° C. primarily leads to alkyl-hydroperoxides, dialkylperoxides, alcohols, ketones; as well as the products which result from cleavage of dihydroperoxides such as diketones, keto-aldehydes hydroxyketones and so forth. At higher temperatures (above 120° C.) the reaction rates are increased and cleavage of the hydroperoxides plays a more important role. Additionally, at the higher temperatures, the viscosity of the bulk medium increases as a result of the polycondesation of the difunctional oxygenated products formed in the primary oxidation phase. Further polycondesation and polymerization reaction of these high molecular weight intermediates results in products which are no longer soluble in the hydrocarbon and form varnish like deposits and sludge.

Since autoxidation is a free-radical chain reaction, it therefore, can be inhibited at the initiation and/or propagation steps. Typical oxidation inhibition by diarylamines, such as dialkyldiphenylamine and N-phenyl-α-napthylamine, also involves radical scavenging. The transfer of hydrogen from the NH group of the amine to the peroxide radicals results in the formation of a diarylamino radical which is resonance stabilized, thus prevents new chains from forming. A secondary peroxy radical or hydroperoxide can react with the diarylamino radical to form the nitroxy radical, which is also a very potent inhibitor. Increased demands have been placed on many functional fluids which have in-turn placed emphasis on new inhibitors.

The present invention is directed in part to aryl-amino bridged benzo[b]perhydroheterocyclic compounds particularly useful as stabilizers. The compounds may serve as antioxidants, antiozoants, heat stabilizers and ultraviolet light stabilizers and such compounds are oil soluble, thus particularly suited for use an antioxidant in a lubricating oil composition. Disclosed are particularly suited resonance stabilized inhibitor compounds according to formula I:

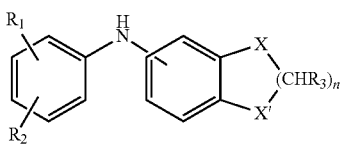

Formula I wherein: $R_1$ and $R_2$ are each independently selected from the group consisting of hydrogen, alkyl from 1 to 20 carbon atoms, —OR, —SR and —NRR', where R and R' are independently hydrogen or alkyl from 1 to 6 carbon atoms, or $R_1$ and $R_2$ when adjacent to each other together from a 5 to 6 member ring, said ring is selected from a 5 to 6 membered alicyclic ring and a 5 to 6 membered aromatic ring, wherein said ring may be unsubstituted or substituted with 1 or 2 alkyl groups each having from 1 to 20 carbon atoms; each $R_3$ is hydrogen or alkyl from 1 to 6 carbon atoms, X and X' are independently selected from —$CHR_4$—, oxygen, sulfur or $NR_5$, wherein $R_4$ and $R_5$ are independently hydrogen or alkyl from 1 to 6 carbon atoms, with the proviso that at least one of X or X' is a heteroatom positioned ortho or para to the bridging nitrogen atom, and further provided that when one of X or X' is —$CHR_4$— then the other may not be oxygen, and when X or X' are nitrogen then $R_1$ or $R_2$ is not hydroxyl; and n is an integer from 1 to 2. Nitrogen is a particularly preferred heteroatom, which is more preferred than oxygen, which both are more preferred than sulfur. Improved resonance stabilization may be accomplished by substituents on the rings, thus particularly preferred groups are electron donating groups, more so when positioned ortho and para positions to the bridging nitrogen atom, thereby stabilizing this amino radical. Therefore, one aspect of the present invention is directed to where at least one $R_1$ and $R_2$ is —OR, —SR or —NRR' with —NRR' being preferred. In another aspect, there is only a single substituent on the aryl group, thus $R_1$ is hydrogen with $R_2$ selected from —OR, —SR or —NRR' with —NRR' being preferred; wherein R and R' are defined herein above and even more preferred, R is alkyl from 1 to 6 carbon atoms.

By way of an example, when X is selected to be the heteroatom, the ortho and para positions of X to the bridging nitrogen atom are depicted below.

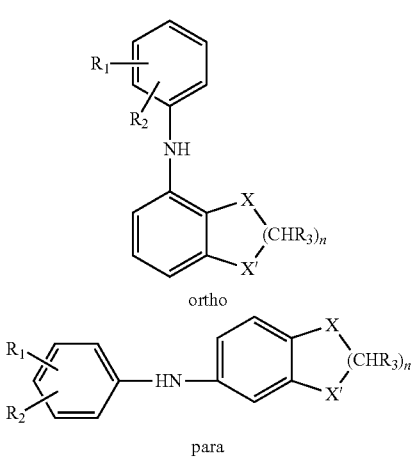

The requirement for the ortho and para position are more prevalent when X' is $CHR_4$— which is a preferred embodiment. Additionally, $R_1$ and $R_2$, when other than hydrogen, are preferably positioned so that at least one is in the ortho or para position to the bridging nitrogen atom.

In one preferred aspect, $R_1$ is hydrogen and $R_2$ is selected from the group consisting of alkyl from 1 to 20 carbon atoms, —OR, —SR and —NRR', where R and R' are independently hydrogen or alkyl from 1 to 6 carbon atoms; also preferred in the above, is where R is alkyl from 1 to 6. Preferably in the above, $R_2$ is positioned in the ortho or para position to the bridging nitrogen atom. Alkyl chains have demonstrated improved oil solubility in the resulting compound, therefore straight and branched chain alkyl from 3 to 18 carbon atoms are particularly preferred when the compounds are employed in lubricating oil compositions. Nitrogen and oxygen heterocycles have demonstrated robust properties and thus, preferably at least one X or X' contains a nitrogen or oxygen atom, with nitrogen being particularly preferred, with single nitrogen atom heterocycles even more preferred.

In another preferred aspect, $R_1$ and $R_2$ are each independently selected from the group consisting of alkyl from 1 to 20 carbon atoms, —OR, —SR and —NRR', where R is alkyl from 1 to 6 carbon atoms and R' is hydrogen or alkyl from 1 to 6 carbon atoms. In another aspect, when $R_1$ and $R_2$ are located on adjacent carbon atoms, $R_1$ and $R_2$ together can form a 5 to 6 membered alicyclic or aromatic ring which may be unsubstituted or substituted with 1 or 2 alkyl groups each having from 1 to 20 carbon atoms, preferably alkyl for 3 to 18 carbon atoms. Preferably at least one X or X' contains a nitrogen or oxygen atom, with nitrogen being particularly preferred, with single nitrogen atom heterocycles even more preferred.

In formula I, particularly preferred compounds are depicted when at least one X and X' is selected from nitrogen or oxygen and even more preferred is when at least one X and X' is nitrogen. These nitrogen containing benzo[b]perhydroheterocyclic compounds are further defined according to formula II Accordingly, particularly preferred compounds are depicted by the Formula II below:

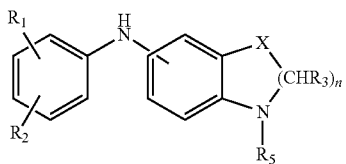

Formula II wherein $R_1$, $R_2$, $R_3$, $R_5$, X and n, are defined herein above, with the proviso the heterocyclic nitrogen is positioned ortho or para to the bridging nitrogen atom and further providing that when X is —$CHR_4$— then $R_1$ and $R_2$ are not hydroxyl. As stated above, alkyl substituents have been employed to improve oil solubility and are particularly useful when there is greater than two heteroatoms in the compound. Preferably, if the compound is to contain alkyl groups, the alkyl groups are characterized in regard with $R_1$ or $R_2$. Thus preferably at least one $R_1$ and $R_2$ are alkyl from 1 to 20 carbon atoms, —OR, —SR and —NRR', where R is alkyl from 1 to 6 carbon atoms and R' is defined above. Additionally, solubility may be increased in respect to $R_1$ and $R_2$ when $R_1$ and $R_2$ are adjacent to each other and can form a 5 to 6 membered alicyclic or aromatic ring which is substituted with 1 or 2 alkyl groups each having from 1 to 20 carbon atoms. Even more preferred is that each $R_3$ and $R_4$ when selected are all hydrogen.

Particularly preferred compounds of Formula II are depicted when n is equal to two. Even more preferred are the tetrahydro-quinolines, thus X is —$CHR_4$— and the bridging ring nitrogen is attached at the 6 or 8 position.

In Formula I, when n=1, the compounds can be depicted by Formula Ia below:

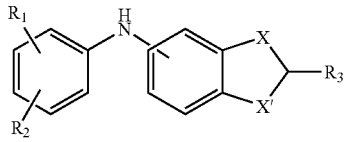

Formula Ia wherein: $R_1$ and $R_2$ are each independently selected from the group consisting of hydrogen, alkyl from 1 to 20 carbon atoms, —OR, —SR and —NRR', where R and R' are independently hydrogen or alkyl from 1 to 6 carbon atoms, or $R_1$ and $R_2$ when adjacent to each other together form a 5 or 6 membered alicyclic or aromatic ring which may be unsubstituted or substituted with 1 or 2 alkyl groups each having from 1 to 6 carbon atoms; $R_3$ is hydrogen or alkyl from 1 to 6 carbon atoms; X is oxygen, sulfur, —NH— or —N(alk)- where alk is alkyl from 1 to 6 carbon atoms with the proviso that the X heteroatom is positioned ortho or para to the bridging nitrogen atom; X' is selected from —$CHR_4$—, oxygen, sulfur or $NR_5$, wherein $R_4$ and $R_5$ are independently hydrogen or alkyl from 1 to 6 carbon atoms, with the proviso that when X is oxygen then X' is oxygen, sulfur or $NR_5$. Particularly suited benzo[b]perhydeoheterocyclic moieties include substituted and unsubstituted: 2,3-dihydro-indole, 2,3-dihydro-benzo[b]thiophene, 2,3-dihydro-benzoimidazole including alkyl and dialkyl substituted dihydro-benzoimidazoles, 2,3dihydrobenzooxazole, 2,3-dihydro-benzothiazole, benzo[1,3]dithiole, benzo[1,3]oxathiole and benzo[1,3]dioxole.

In Formula I, when n=2, particularly useful heterocyclic rings are selected from substituted and unsubstituted heterocyclic rings consisting of the group: 1,2,3,4-tetrahydroquinoline; 1,2,3,4-tetrahydroqinoxaline; 3,4-dihydro-2H-benzo[1,4]thiazine; 3,4-dihydro-2H-benzo[1,4]oxazine; thiochroman, 2,3-dihydro-benzo[1,4]dithiine; 2,3-dihydrobenzo[1,4]oxathiine; 2,3-dihydro-benzo[1,4]dioxine and chroman.

Particularly suited compounds of the present invention are exemplified herein below, therefore, another aspect of the present invention is directed to the compounds comprising: phenyl-(1,2,3,4-tetrahydro-quinolin-6-yl)-amine; -(4-tert-butylphenyl)-1,2,3,4-tetrahydroquinolin-8-amine; N-2-naphthyl-1,2,3,4-tetrahydroquinolin-6-amine; N-2-naphthyl-1,2,3,4-tetrahydroquinolin-8-amine; N-(4-tert-butylphenyl)-2,3-dihydro-1-benzofuran-5-amine; N'-(2,3-dihydro-1-benzofuran-5-yl)-N,N-diethylbenzene-1,4-diamine; N-(4-tert-butylphenyl)-2,3-dihydro-1,4-benzodioxin-6-amine; N-(4-butylphenyl)-1,2,3,4-tetrahydroquinolin-8-amine.

The compounds of Formula I are particularly useful when employed in a lubricating composition comprising the compound of Formula I with an oil of lubricating viscosity.

The lubricant compositions of this invention include a major amount of base oil of lubricating viscosity. Base Oil as used herein is defined as a base stock or blend of base stocks which is a lubricant component that is produced by a single manufacturer to the same specifications (independent of feed source or manufacturer's location): that meets the same manufacturer's specification; and that is identified by a unique formula, product identification number, or both. Base stocks may be manufactured using a variety of different processes including but not limited to distillation, solvent refining, hydrogen processing, oligomerization, esterification, and rerefining. Rerefined stock shall be substantially free from materials introduced through manufacturing, contamination, or previous use. The base oil of this invention may be any natural or synthetic lubricating base oil fraction particularly those having a kinematic viscosity at 100 degrees Centigrade (C) and about 5 centistokes (cSt) to about 20 cSt, preferably about 7 cSt to about 16 cSt, more preferably about 9 cSt to about 15 cSt. Hydrocarbon synthetic oils may include, for example, oils prepared from the polymerization of ethylene, i.e., polyalphaolefin or PAO, or from hydrocarbon synthesis procedures using carbon monoxide and hydrogen gases such as in a Fisher-Tropsch process. A preferred base oil is one that comprises little, if any, heavy fraction; e.g., little, if any, lube oil fraction of viscosity 20 cSt or higher at 100 degrees C.

The base oil may be derived from natural lubricating oils, synthetic lubricating oils or mixtures thereof. Suitable base oil includes base stocks obtained by isomerization of synthetic wax and slack wax, as well as hydrocrackate base stocks produced by hydrocracking (rather than solvent extracting) the aromatic and polar components of the crude. Suitable base oils include those in all API categories I, II, III, IV and V as defined in API Publication 1509, 14th Edition, Addendum I, December 1998. Saturates levels and viscosity indices for Group I, II and III base oils are listed in Table 1. Group IV base oils are polyalphaolefins (PAO). Group V base oils include all other base oils not included in Group I, II, III, or IV. Although Group II, III and IV base oils are preferred for use in this invention, these preferred base oils may be prepared by combining one or more of Group I, II, III, IV and V base stocks or base oils.

TABLE 1

Saturates, Sulfur and Viscosity Index of Group I, II and III Base Stocks

| Group | Saturates (As determined by ASTM D 2007) Sulfur (As determined by ASTM D 2270) | Viscosity Index (As determined by ASTM D 4294, ASTM D 4297 or ASTM D 3120) |
|---|---|---|
| I | Less than 90% saturates and/or Greater than to 0.03% sulfur | Greater than or equal to 80 and less than 120 |
| II | Greater than or equal to 90% saturates and less than or equal to 0.03% sulfur | Greater than or equal to 80 and less than 120 |
| III | Greater than or equal to 90% saturates and less than or equal to 0.03% sulfur | Greater than or equal to 120 |

Natural lubricating oils may include animal oils, vegetable oils (e.g., rapeseed oils, castor oils and lard oil), petroleum oils, mineral oils, and oils derived from coal or shale.

Synthetic oils may include hydrocarbon oils and halo-substituted hydrocarbon oils such as polymerized and interpolymerized olefins, alkylbenzenes, polyphenyls, alkylated diphenyl ethers, alkylated diphenyl sulfides, as well as their derivatives, analogues and homologues thereof, and the like. Synthetic lubricating oils also include alkylene oxide polymers, interpolymers, copolymers and derivatives thereof wherein the terminal hydroxyl groups have been modified by esterification, etherification, etc. Another suitable class of synthetic lubricating oils comprises the esters of dicarboxylic acids with a variety of alcohols. Esters useful as synthetic oils also include those made from $C_5$ to $C_{12}$ monocarboxylic acids and polyols and polyol ethers. Tri-alkyl phosphate ester oils such as those exemplified by tri-n-butyl phosphate and tri-iso-butyl phosphate are also suitable for use as base oils.

Silicon-based oils (such as the polyakyl-, polyaryl-, polyalkoxy-, or polyaryloxy-siloxane oils and silicate oils) comprise another useful class of synthetic lubricating oils. Other synthetic lubricating oils include liquid esters of phosphorus-containing acids, polymeric tetrahydrofurans, polyalphaolefins, and the like.

The base oil may be derived from unrefined, refined, rerefined oils, or mixtures thereof. Unrefined oils are obtained directly from a natural source or synthetic source (e.g., coal, shale, or tar sand bitumen) without further purification or treatment. Examples of unrefined oils include a shale oil obtained directly from a retorting operation, a petroleum oil obtained directly from distillation, or an ester oil obtained directly from an esterification process, each of which may then be used without further treatment. Refined oils are similar to the unrefined oils except that refined oils have been treated in one or more purification steps to improve one or more properties. Suitable purification techniques include distillation, hydrocracking, hydrotreating, dewaxing, solvent extraction, acid or base extraction, filtration, and percolation, all of which are known to those skilled in the art. Rerefined oils are obtained by treating used oils in processes similar to those used to obtain the refined oils. These rerefined oils are also known as reclaimed or reprocessed oils and often are additionally processed by techniques for removal of spent additives and oil breakdown products.

Base oil derived from the hydroisomerization of wax may also be used, either alone or in combination with the aforesaid natural and/or synthetic base oil. Such wax isomerate oil is produced by the hydroisomerization of natural or synthetic waxes or mixtures thereof over a hydroisomerization catalyst.

It is preferred to use a major amount of base oil in the lubricating oil of this invention. A major amount of base oil as defined herein comprises 40 wt. % or more. Preferred amounts of base oil comprise about 40 wt. % to about 97 wt. % of at least one of Group II, III and IV base oil or preferably greater than about 50 wt. % to about 97 wt. % of at least one of Group II, III and IV base oil or more preferably about 60 wt. % to about 97 wt. % of at least one of Group II, III and IV base oil. (When wt. % is used herein, it is referring to wt. % of the lubricating oil unless otherwise specified.) A more preferred embodiment of this invention may comprise an amount of base oil that comprises about 85 wt. % to about 95 wt. % of the lubricating oil.

The amount of benzo[b]perhydroheterocyclic compounds of the present invention in the lubricating oil composition will be in a minor amount compared to the base oil of lubricating viscosity. Generally, it will be in an amount from about 0.01 to 10 wt %, preferably from about 0.1 to about 2.0 wt %, more preferably from about 0.3 to about 1.8 wt % and even more preferably from about 0.5 to about 1.5 wt %, based on the total weight of the lubricating oil composition.

The following additive components are examples of components that can be favorably employed in combination with the lubricating additive of the present invention. These examples of additives are provided to illustrate the present invention, but they are not intended to limit it.

(A) Ashless dispersants: alkenyl succinimides, alkenyl succinimides modified with other organic compounds such as ethylene carbonate, polysuccinimides, and alkenyl succinimides modified with boric acid, alkenyl succinic ester.

(B) Oxidation inhibitors:

1) Phenol type phenolic oxidation inhibitors: 4,4'-methylenebis(2,6-di-tert-butylphenol), 4,4'-bis(2,6-di-tert-butylphenol), 4,4'-bis(2-methyl-6-tert-butylphenol), 2,2'-(methylenebis(4-methyl-6-tert-butyl-phenol)), 4,4'-butylidenebis(3-methyl-6-tert-butylphenol), 4,4'-isopropylidenebis(2,6-di-tert-butylphenol), 2,2'-methylenebis(4-methyl-6-nonylphenol), 2,2'-isobutylidenebis(4,6-dimethylphenol), 2,2'-methylenebis(4-methyl-6-cyclohexylphenol), 2,6-di-tert-butyl-4-methylphenol, 2,6-di-tert-butyl-4-ethylphenol, 2,4-dimethyl-6-tert-butyl-phenol, 2,6-di-tert-α-dimethylamino-p-cresol, 2,6-di-tert-4(N,N' dimethylaminomethylphenol),4,4'-thiobis(2-methyl-6-tert-butylphenol), 2,2'-thiobis(4-methyl-6-tert-butylphenol), bis(3-methyl-4-hydroxy-5-tert-butylbenzyl)-sulfide, and bis(3,5-di-tert-butyl-4-hydroxybenzyl).

2) Other types: metal dithiocarbamate (e.g., zinc dithiocarbamate), and methylenebis(dibutyldithiocarbamate).

(C) Rust inhibitors (Anti-rust agents):

1) Nonionic polyoxyethylene surface active agents: polyoxyethylene lauryl ether, polyoxyethylene higher alcohol ether, polyoxyethylene nonylphenyl ether, polyoxyethylene octylphenyl ether, polyoxyethylene octyl stearyl ether, polyoxyethylene oleyl ether, polyoxyethylene sorbitol monostearate, polyoxyethylene sorbitol mono-oleate, and polyethylene glycol monooleate.

2) Other compounds: stearic acid and other fatty acids, dicarboxylic acids, metal soaps, fatty acid amine salts, metal salts of heavy sulfonic acid, partial carboxylic acid ester of polyhydric alcohol, and phosphoric ester.

(D) Demulsifiers: addition product of alkylphenol and ethyleneoxide, polyoxyethylene alkyl ether, and polyoxyethylene sorbitane ester.

(E) Extreme pressure agents (EP agents), sulfurized oils, diphenyl sulfide, methyl trichlorostearate, chlorinated naphthalene, benzyl iodide, fluoroalkylpolysiloxane, and lead naphthenate.

(F) Friction modifiers: fatty alcohol, fatty acid, amine, borated ester, and other esters (G) Multifunctional additives: sulfurized oxymolybdenum dithiocarbamate, sulfurized oxymolybdenum organo phosphorodithioate, oxymolybdenum monoglyceride, oxymolybdenum diethylate amide, amine-molybdenum complex compound, and sulfur-containing molybdenum complex compound (H) Viscosity Index improvers: polymethacrylate type polymers, ethylene-propylene copolymers, styrene-isoprene copolymers, hydrated styrene-isoprene copolymers, polyisobutylene, and dispersant type viscosity index improvers.

(I) Pour point depressants: polymethyl methacrylate.

(K) Foam Inhibitors: alkyl methacrylate polymers and dimethyl silicone polymers.

(L) Wear inhibitors: zinc dialkyldithiophosphate (Zn-DTP, primary alkyl type & secondary alkyl type).

General Synthetic Procedures

The benzo[b]perhydroheterocyclic arylamines of this invention may be prepared by the following general methods and procedures. It should be appreciated that where typical or preferred process conditions (e.g., reaction temperatures, times, mole ratios of reactants, solvents, pressures, etc.) are given; other process conditions may also be used unless otherwise stated. Optimum reaction conditions may vary with the particular reactants or solvents used, but such conditions can be determined by one skilled in the art by routine optimization procedures.

Those skilled in the art will also recognize that it may be necessary to block or protect certain functional groups while conducting the following synthetic procedures. In such cases, the protecting group will serve to protect the functional group from undesired reactions or to block its undesired reaction with other functional groups or with the reagents used to carry out the desired chemical transformations. The proper choice of a protecting group for a particular functional group will be readily apparent to one skilled in the art. Various protecting groups and their introduction and removal are described, for example, in T. W. Greene and P. G. M. Wuts, *Protective Groups in Organic Synthesis*, Second Edition, Wiley, New York, 1991, and references cited therein.

Synthesis

The benzo[b]perhydroheterocyclic arylamines of the present invention are prepared by reduction of benzo[b]heterocyclic arylamines as illustrated in sequence (I).

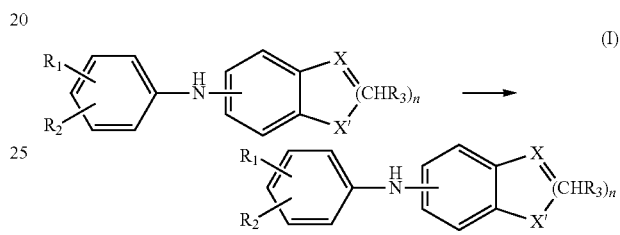

The benzo[b]heterocyclic arylamines may be prepared by the reaction sequences depicted in (II) and (III)

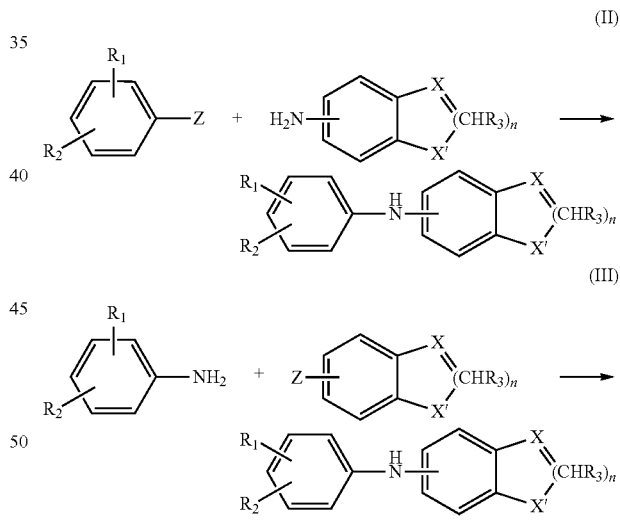

wherein $R_1$, $R_2$, $R_3$, n, X and X' are as defined herein and Z is —OH, —$NH_2$, Cl, Br or I.

The coupling reactions shown in (II) and (III) are known in the art for the synthesis of diphenylamines. These coupling methods are applicable to the synthesis of benzo[b]heterocyclic arylamines. Particularly noteworthy coupling reactions for the synthesis of anilinoquinolines are described by Buu-Hoi, Royer and Hubert-Habart, *J. Chem. Soc.*, 1956, 2048-2051 and Okada, Suzuki, Hirose, Toda and Ozawa, *Chem. Commun.*, 2001, 2492-2493. Buchwald and Hartwig have developed a palladium catalyzed coupling of aromatic amines and aromatic halides which is applicable to the synthesis of benzo[b]heterocyclic arylamines (Wolfe, Wagaw, Marcoux and Buchwald, *Acc. Chem. Res.*, 1998, 805-818 and references cited therein and J. C. Peters, S. B. Harkins, S. D. Brown and M. D W. Day, *Inorg. Chem.*, 2001, 40, 5083-5091). A copper catalyzed method has been developed by Patil, Kelkar, Nabi, and Chaudhari, *Chem. Commun.*, 2003, 2460-2461.

There are several methods to reduce the benzo[b]heterocyclic arylamines to benzo[b]perhydroheterocyclic arylamines. The methods that can be employed are the same as those for the reduction of quinoline to tetrahydroquinoline provided that any functionality which is sensitive towards reduction is protected. Hydrogenation can be used as described for quinolines in Rylander, *Catalytic Hydrogenation in Organic Synthesis*, 1979, 213-230, Academic Press. Hydrogenation of quinolines to tetrahydroquinolines as well as other methods of reduction is described in Hudlicky, *Reductions in Organic Chemistry Second Edition*, 1996, 72-74, American Chemical Society. 6-aminoquinoline has been hydrogenated to 6-aminotetrahydroquinoline with a platinum oxide catalyst in Example 2 of WO 92/05173. The reduction of quinolines to tetrahydroquinolines with sodium borohydride—nickelous chloride is described by Nose and Kudo, *Chem. Pharm. Bull.*, 1984, 32, 2421-2425. The reduction of quinolines to tetrahydroquinolines with sodium borohydride in acidic media is described by Gribble and Heald, *Synthesis*, 1975, 650-652.

EXAMPLES

The invention is further illustrated by the following examples, which are not to be considered as limitative of its scope. A further understanding of the invention can be had in the following nonlimiting Preparations and Examples. Wherein unless expressly stated in the contrary, all temperatures and temperatures ranges refer to the Centigrade system and the term "ambient" or "room temperature" refers to about 20 to 25° C. The term "percent or %" refers to weight percent, and the term "mole" or "moles" refers to gram moles. The term "equivalent" refers to a quantity of reagent equal in moles, to the moles of the preceding or succeeding reactant recited in that example in terms of finite moles or finite weight or volume. Where given, proton-magnetic resonance spectrum (p.m.r. or n.m.r) were determined at 300 mHz, signals are assigned as singlets(s), braod singlets (bs), doublets (d), double doublets (dd), triplets (t), double triplets (dt), quartets (q), and multiplets (m), and cps refers to cycles per second.

Example 1

Preparation of Phenyl-(1,2,3,4-tetrahydro-quinolin-6-yl)-amine

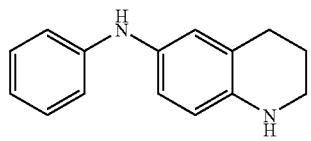

A solution of 20.4 grams of 6-anilinoquinoline (prepared as described in Buu-Hoi, Royer and Hubert-Habart, *J. Chem. Soc.*, 1956, 2048-2051) in 400 mL of acetic acid containing 1.3 grams of platinum(IV) oxide was hydrogenated at 30 psi for 4.2 hours on a Parr low-pressure hydrogenator. The solution was filtered; and the filtrate was neutralized with 6N aqueous sodium hydroxide. The aqueous phase was extracted three times with dichloromethane. The combined dichloromethane layers were washed with 6N aqueous sodium hydroxide followed by brine. The dichloromethane layer was dried over anhydrous magnesium sulfate, filtered and concentrated in vacuo to yield 20.4 grams of a dark residue. The dark residue was recrystallized from 95% ethanol to yield 15.2 grams of the desired product as a grey solid. $^1$H NMR (CDCl$_3$) δ 7.2 (m, 2H), 6.8 (m, 4H), 6.45 (d, 1H), 5.35 (bs, 1H), 3.4 (bs, 1H), 3.25 (t, 2H), 2.75 (t, 2H), 1.95 (p, 2H).

Example 2

Step A—Preparation of N-(4-tert-butylphenyl)quinolin-8-amine

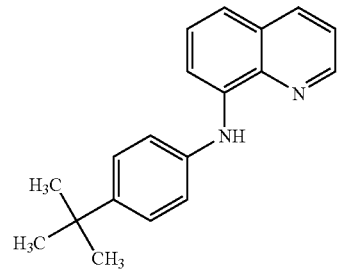

To a flask equipped with a magnetic stirrer, reflux condensor, and nitrogen inlet was added 8-aminoquinoline (14.4 grams, 0.10 moles), 4-tert-butyl bromobenzene (21.3 grams, 0.10 moles), tris(dibenzylideneacetone)dipalladium (0) (1.8 grams, 0.002 moles), rac-2,2'-bis(diphenylphosphino)-1,1'-binapthyl (2.5 grams, 0.004 moles), sodium tert-butoxide (19.4 grams, 0.20 moles) and anhydrous toluene (150 mL). The contents of the flask were refluxed for four days; cooled to room temperature; and filtered through a pad of silica gel. The silica gel pad was then eluted with dichloromethane (240 mL). The combined organic layers were concentrated in vacuo to yield a dark blue solid. The solid was chromatographed on silica gel, eluting with hexane/ethyl acetate (20:1) to afford 23 grams of the desired product as a yellow solid. $^1$H NMR (CDCl$_3$) □ 8.8 (m, 1H), 8.2 (bs, 1H), 8.1 (d, 1H), 7.1-7.5 (m, 9H), 1.35 (s, 9H).

Step B—Preparation of N-(4-tert-butylphenyl)-1,2,3,4-tetrahydroquinolin-8-amine

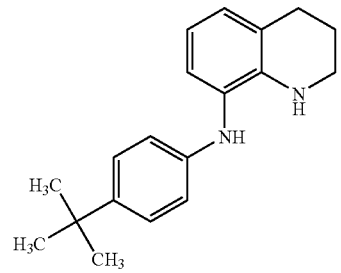

A solution of 2.46 grams of N-(4-tert-butylphenyl)quinolin-8-amine from Step A in 100 mL of acetic acid containing 0.15 grams of platinum(IV) oxide was hydrogenated at 45 psi for 1.5 hours on a Parr low-pressure hydrogenator. The solution was filtered through diatomaceous earth; concentrated in vacuo; and neutralized with 3N aqueous sodium hydroxide. The aqueous phase was diluted with water and extracted three times with ethyl acetate. The combined ethyl acetate layers were washed with brine; dried over anhydrous magnesium sulfate, filtered and concentrated in vacuo to yield 2.5 grams of dark blue oil. The oil was chromatographed on silica gel, eluting with hexane/ethyl acetate (20:1) to afford 2.0 grams of the desired product as a yellow oil. $^1$H NMR (CDCl$_3$) δ 7.2 (d, 2H), 6.5-6.95 (m, 5H), 4.95 (bs, 1H), 3.3 (t, 2H), 2.8 (t, 2H), 1.9 (p, 2H), 1.3 (s, 9H).

Example 3

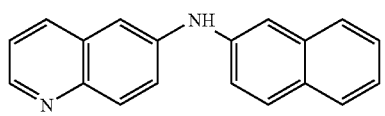

Step A—Preparation of
N-2-naphthylquinolin-6-amine

To a flask equipped with a magnetic stirrer, reflux condensor, and nitrogen inlet was added 6-aminoquinoline (6.69 grams, 46.4 mmoles), 2-bromonapthalene (9.15 grams, 44.2 mmoles), tris(dibenzylideneacetone)dipalladium (0) (0.80 grams, 0.87 mmoles), rac-2,2'-bis(diphenylphosphino)-1,1'-binapthyl (1.10 grams, 1.77 mmoles), sodium tert-butoxide (8.49 grams, 88.3 mmoles) and anhydrous toluene (90 mL). The contents of the flask were refluxed for five hours; cooled to room temperature; and filtered through a pad of silica gel. The silica gel pad was then eluted with tetrahydrofuran (135 mL). The combined organic layers were concentrated in vacuo to yield a brown solid. The solid was recrystallized from ethanol to afford 8.6 grams of the desired product as a yellow solid. $^1$H NMR (DMSO-d$_6$/D$_2$O) δ 8.9 (d, 1H), 8.65 (d, 1H), 8.2 (d, 1H), 7.25-8.05 (m, 10H).

Step B—Preparation of
N-2-naphthyl-1,2,3,4-tetrahydroquinolin-6-amine

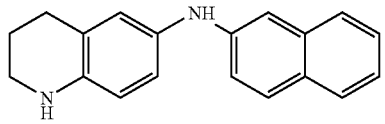

A solution of 7.00 grams of N-2-naphthylquinolin-6-amine from above in acetic acid (60 mL) and ethyl acetate (10 mL) containing 0.55 grams of platinum(IV) oxide was hydrogenated at 45 psi for 6.0 hours on a Parr low-pressure hydrogenator. The solution was filtered through diatomaceous earth; concentrated in vacuo; and neutralized with 3N aqueous sodium hydroxide. The aqueous phase was diluted with water and extracted three times with ethyl acetate. The combined ethyl acetate layers were washed with brine; dried over anhydrous magnesium sulfate, filtered and concentrated in vacuo to yield 5.5 grams solid. The solid was chromatographed on silica gel, eluting with hexane/ethyl acetate gradient to afford 3.5 grams of the desired product as a yellow solid. $^1$H NMR (CDCl$_3$/D$_2$O) δ 6.4-7.8 (m, 10H), 3.1-3.5 (m, 2H), 2.6-2.9 (m, 2H), 1.95 (p, 2H).

Example 4

Step A—Preparation of
N-2-naphthylquinolin-8-amine

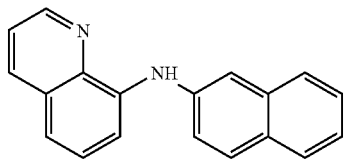

To a flask equipped with a magnetic stirrer, reflux condensor, and nitrogen inlet was added 8-aminoquinoline (6.81 grams, 47.2 mmoles), 2-bromonapthalene (9.58 grams, 46.3 mmoles), tris(dibenzylideneacetone)dipalladium (0) (0.84 grams, 0.92 mmoles), rac-2,2'-bis(diphenylphosphino)-1,1'-binapthyl (0.6 grams, 0.92 mmoles), sodium tert-butoxide (8.86 grams, 92.2 mmoles) and anhydrous toluene (90 mL). The contents of the flask were refluxed for sixteen hours; cooled to room temperature; and filtered through a pad of silica gel. The silica gel pad was then eluted with dichloromethane (135 mL). The combined organic layers were concentrated in vacuo to yield a yellow solid. The solid was chromatographed on silica gel, eluting with a hexane/ethyl acetate gradient to afford 6.6 grams of the desired product as a yellow solid. $^1$H NMR (CDCl$_3$) δ 8.75 (d, 1H), 8.4 (bs, 1H), 8.05 (d, 1H), 7.6-7.9 (m, 5H), 7.25-7.5 (m, 5H), 7.2 (d, 1H).

Step B—Preparation of
N-2-naphthyl-1,2,3,4-tetrahydroquinolin-8-amine

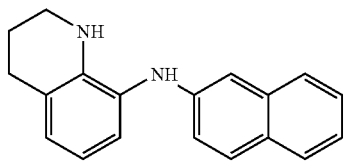

A solution of 4.08 grams of N-2-naphthylquinolin-8-amine from above in acetic acid (10 mL) and ethyl acetate (150 mL) containing 0.24 grams of platinum(IV) oxide was hydrogenated at 45 psi for four hours on a Parr low-pressure hydrogenator. The solution was filtered through diatomaceous earth; concentrated in vacuo; and neutralized with 3N aqueous sodium hydroxide. The aqueous phase was diluted with water and extracted three times with ethyl acetate. The combined ethyl acetate layers were washed with brine; dried over anhydrous magnesium sulfate, filtered and concentrated in vacuo to yield 4.2 grams of the desired product as a purple oil. $^1$H NMR (CDCl$_3$/D$_2$O) δ 7.7 (m, 2H), 7.6 (d, 1H), 7.35 (t, 1H), 7.25 (m, 1H), 7.05 (m, 2H), 6.9 (m, 2H), 6.6 (t, 1H), 3.3 (t, 2H), 2.85 (t, 2H), 1.95 (p, 2H).

Example 5

Preparation of N-(4-tert-butylphenyl)-2,3-dihydro-1-benzofuran-5-amine

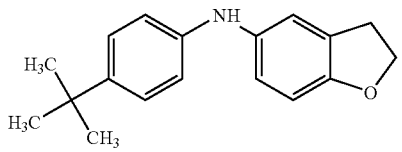

To a flask equipped with a magnetic stirrer, reflux condensor, and nitrogen inlet was added 2,3-dihydro-1-benzofuran-5-amine (11.6 grams, 85.8 mmoles, prepared as in Example 23 of U.S. Pat. No. 20040029932), 4-tert-butyl bromobenzene (18.1 grams, 85 mmoles), tris(dibenzylideneacetone)dipalladium (0) (1.6 grams, 1.7 mmoles), rac-2,2'-bis(diphenylphosphino)-1,1'-binapthyl (2.1 grams, 3.4 mmoles), sodium tert-butoxide (16.4 grams, 0.17 moles) and anhydrous toluene (100 mL). The contents of the flask were refluxed for three days; cooled to room temperature; and filtered through a pad of silica gel. The silica gel pad was then eluted with dichloromethane (150 mL). The combined organic layers were concentrated in vacuo to yield a dark solid. The solid was chromatographed on silica gel, eluting with hexane/ethyl acetate (20:1) to afford 10 grams of the desired product as a white solid. $^1$H NMR (CDCl$_3$) δ 7.25 (d, 2H), 6.95 (s, 1H), 6.85 (d, 3H), 6.7 (d, 1H), 5.4 (bs, 1H), 4.5 (t, 2H), 3.15 (t, 2H), 1.3 (s, 9H).

Example 6

Preparation of N'-(2,3-dihydro-1-benzofuran-5-yl)-N,N-diethylbenzene-1,4-diamine

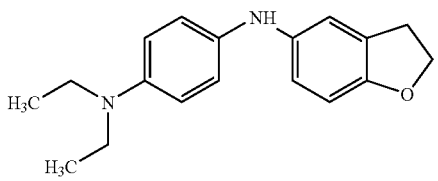

To a flask equipped with a magnetic stirrer, reflux condensor, and nitrogen inlet was added N,N-diethyl-1,4-phenylenediamine (3.35 grams, 20.4 mmoles), 5-bromo-2,3-dihydrobenzofuran (3.4 grams, 17.1 mmoles), tris(dibenzylideneacetone)dipalladium (0) (0.39 grams, 0.43 mmoles), rac-2,2'-bis(diphenylphosphino)-1,1'-binapthyl (2.1 grams, 3.4 mmoles), sodium tert-butoxide (0.71 grams, 1.28 mmoles) and anhydrous toluene (90 mL). The contents of the flask were heated to 80° C. for two days; cooled to room temperature; and filtered through a pad of silica gel. The silica gel pad was then eluted with dichloromethane (200 mL). The combined organic layers were concentrated in vacuo to yield a dark blue oil. The oil was chromatographed on silica gel, eluting with a hexane/ethyl acetate gradient to afford 4.2 grams of the desired product as a brown oil. $^1$H NMR (CDCl$_3$) δ 6.6-7.0 (m, 7H), 5.15 (bs, 1H), 4.5 (t, 2H), 3.05-3.2 (m, 6H), 1.1 (t, 6H).

Example 7

Preparation of N-(4-tert-butylphenyl)-2,3-dihydro-1,4-benzodioxin-6-amine

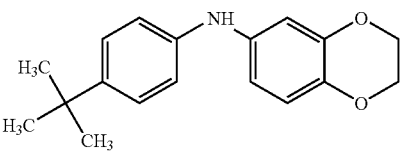

To a flask equipped with a magnetic stirrer, reflux condensor, and nitrogen inlet was added 1,4-benzodioxin-6-amine (5.26 grams, 34.8 mmoles), 4-tert-butyl bromobenzene (6.83 grams, 32.1 mmoles), tris(dibenzylideneacetone)dipalladium (0) (0.58 grams, 0.6 mmoles), rac-2,2'-bis(diphenylphosphino)-1,1'-binapthyl (0.79 grams, 1.2 mmoles), sodium tert-butoxide (6.08 grams, 63.0 mmoles) and anhydrous toluene (70 mL). The contents of the flask were refluxed for three days; cooled to room temperature; and filtered through a pad of silica gel. The silica gel pad was then eluted with dichloromethane (300 mL). The combined organic layers were concentrated in vacuo to yield a dark solid. The solid was chromatographed on silica gel, eluting with a hexane/ethyl acetate gradient to afford 5 grams of the desired product as a white solid. $^1$H NMR (CDCl$_3$) δ 7.25 (d, 2H), 6.9 (d, 2H), 6.75 (d, 1H), 6.5-6.7 (m, 2H), 5.4 (bs, 1H), 4.2 (s, 4H), 1.3 (s, 9H).

Example 8

Preparation of N-(4-butylphenyl)-1,2,3,4-tetrahydroquinolin-8-amine

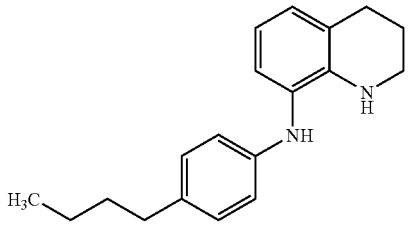

To a flask equipped with a magnetic stirrer, reflux condenser, and nitrogen inlet was added 8-hydroxyquinoline (20.0 grams, 0.14 moles), 4-butyl aniline (24.0 grams, 0.16 moles) and iodine (0.52 grams, 2.0 mmoles). The contents of the flask were refluxed for eight days; cooled to room temperature; and diluted with toluene. The toluene solution was filtered through diatomaceous earth and further diluted with dichloromethane. The solution was washed with 5% aqueous sodium hydroxide three times and water three times. The organic layer was dried over magnesium sulfate, filtered and concentrated in vacuo to yield a dark brown oil. The oil was chromatographed on silica gel, eluting with hexane/ethyl acetate (10:1) to afford 3.7 grams a brown oil.

The oil in 70 mL of acetic acid containing 0.22 grams of platinum(IV) oxide was hydrogenated at 35 psi for 4.5 hours on a Parr low-pressure hydrogenator. The solution was filtered; and the filtrate was neutralized with 6N aqueous sodium hydroxide. The aqueous phase was extracted three times with dichloromethane. The combined dichloromethane layers were washed with 6N aqueous sodium hydroxide followed by brine. The dichloromethane layer was dried over anhydrous magnesium sulfate, filtered and concentrated in vacuo to yield 3.9 grams of a dark brown oil. The oil was chromatographed on silica gel, eluting with a hexane/ethyl acetate gradient to afford 2.1 grams of the desired product as a yellow oil $^1$H NMR (CDCl$_3$) δ 7.05 (d, 2H), 6.95 (d, 1H), 6.80 (d, 1H), 6.70 (d, 2H), 6.6 (t,1H), 4.95 (bs, 1H), 4.05 (bs, 1H), 3.3 (t, 2H), 2.8 (t, 2H), 2.5 (t, 2H), 1.95 (p, 2H), 1.55 (p, 2H), 1.35(h, 2H), 0.95 (t, 3H).

Performance Examples

Oxidation studies of the products of selected Examples were carried out in a bulk oil oxidation bench test as described by E. S. Yamaguchi et al. in Tribology Transactions, Vol. 42(4), 895-901 (1999). In this test the rate of oxygen uptake at constant pressure by a given weight of oil was monitored. The time required (induction time) for rapid oxygen uptake per 25 grams of sample was measured at 171° C. under 1.0 atmosphere of oxygen pressure. The sample was stirred at 1000 revolutions per minute. The results are reported, however, as time for rapid oxygen uptake per 100 grams of sample. The oil contained a catalyst added as oil soluble naphthenates to provide 26 ppm iron, 45 ppm copper, 512 ppm lead, 2.3 ppm manganese, and 24 ppm tin.

The screening formulation was a fully formulation lubricating oil composition and contained in a Group 2+base oil, 7.0 mmoles/kg dialkyl zinc dithiophosphate, 4.0% polyisobutenyl succinimide, 0.5% dinonyldiphenylamine, 0.25% polyisobutenyl succinimide containing 5.5% molybdenum, 48.5 mmoles/kg overbased calcium sulfonate detergent and 0.3% V.I. improver. This baseline screening formulation was tested in the oxidation bench and had a result of 14.1 hours to rapid O$_2$ uptake. To the baseline screening formulation was top treated with an additional compound and tests were performed at two concentrations. The compounds and results of the oxidation bench test are presented in Table 1.

TABLE 1

Oxidation Bench Test of Benzo[b]perhydroheterocyclic compounds

| Performance Example | Compound of Example # | Test Results (Hr to Rapid)O$_2$ uptake (Concentration of Antioxidant) | |
|---|---|---|---|
| | | (0.5 wt %) | (1.0 wt %) |
| 1 | 1 | 55.5 | 125.0 |
| 2 | 2 | 52.9 | 94.5 |
| 3 | 3 | 68.2 | 146.5 |
| 4 | 4 | 80.8 | 152.0 |
| 5 | 5 | 49.0 | 62.0 |
| 6 | 6 | 33.1 | 61.0 |
| 7 | 7 | 44.0 | 68.0 |
| 8 | 8 | 85.0 | 111.0 |
| Comparative A | A[1] | 32.5 | 41.0 |
| Comparative B | B[2] | 41.9 | 83.5 |

A[1] - Irganox ® L57 (diphenylamine alkylated with 2,4,4-trimethylpentene) available commercially from Ciba-Geigy
B[2] - 4-(2-octylamino)diphenylamine available from TCI America The excellent oxidation inhibition performance of Examples 1-8 is demonstrated at 0.5 wt % addition to the base line screening formulation and a 1.0 wt % addition to the base line screening formulation. As can be seen from the Table, there is a dramatic improvement by the addition of a small amount of the compounds of the present invention over the base line screening formulation. More dramatically, is when the compounds in Performance Examples 1-8 is compared to Comparative Example A (a commercially available product) an alkylated diphenylamine, which shows up to a 3× improvement in performance, as shown in the Table. The benzo[b] perhydroheterocyclic amines of the Performance Examples 1-4 and 8 also perform better than the non cyclic amine in Comparative Example B (a commercially available product). The advantages on oxidation inhibition can be seen when constraining a heteroatom into a ring.

What is claimed is:

1. A lubricating oil composition comprising:
a major amount of a base oil of lubricating viscosity from about 40 wt % or more based upon the total lubricating oil composition; and
a compound according to formula I:

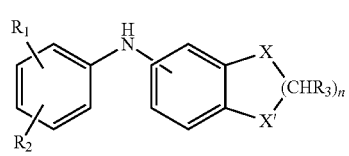

Formula I wherein
R$_1$ and R$_2$ are each independently selected from the group consisting of hydrogen, alkyl from 1 to 20 carbon atoms, —OR, —SR and —NRR', where R and R' are independently hydrogen or alkyl from 1 to 6 carbon atoms, or R$_1$ and R$_2$ when adjacent to each other together form a 5 to 6 membered alicyclic or aromatic ring which may be optionally substituted with 1 or 2 alkyl groups each having from 1 to 20 carbon atoms;
each R$_3$ is hydrogen or alkyl from 1 to 6 carbon atoms,
X and X' are independently selected from —CHR$_4$—, oxygen, sulfur or NR$_5$, wherein R$_4$ and R$_5$ are independently hydrogen or alkyl from 1 to 6 carbon atoms, with the proviso that at least one of X or X' is a heteroatom positioned ortho or para to the bridging nitrogen atom, and when X or X' are nitrogen then R$_1$ or R$_2$ is not hydroxyl; and further provided that when one of X or X' is CHR$_4$— then the other may not be oxygen;
wherein at least one X and X' is sulfur; and
n is an integer from 1 to 2.

2. A lubricating oil composition comprising:
a major amount of a base oil of lubricating viscosity from about 40 wt % or more based upon the total lubricating oil composition; and
a compound according to formula I:

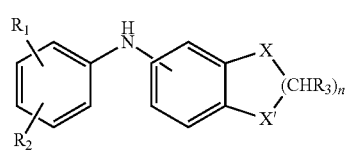

Formula I wherein

R$_1$ and R$_2$ are each independently selected from the group consisting of hydrogen, alkyl from 1 to 20 carbon atoms, —OR, —SR and —NRR', where R and R' are independently hydrogen or alkyl from 1 to 6 carbon atoms, or R$_1$ and R$_2$ when adjacent to each other together form a 5 to 6 membered alicyclic or aromatic ring which may be optionally substituted with 1 or 2 alkyl groups each having from 1 to 20 carbon atoms;

each R$_3$ is hydrogen or alkyl from 1 to 6 carbon atoms, X and X' are independently selected from —CHR$_4$—, oxygen, sulfur or NR$_5$—, wherein R$_4$ and R$_5$ are independently hydrogen or alkyl from 1 to 6 carbon atoms, with the proviso that at least one of X or X' is a heteroatom positioned ortho or para to the bridging nitrogen atom, and when X or X' are nitrogen then R$_1$ or R$_2$ is not hydroxyl; and further provided that when one of X or X' is CHR$_4$— then the other may not be oxygen;

wherein X and X' are independently selected from oxygen, sulfur or NR$_5$, wherein R$_5$ is hydrogen or alkyl from 1 to 6 carbon atoms; and n is an integer from 1 to 2.

3. A lubricating oil composition comprising:

a major amount of a base oil of lubricating viscosity from about 40 wt % or more based upon the total lubricating oil composition; and a compound according to formula I:

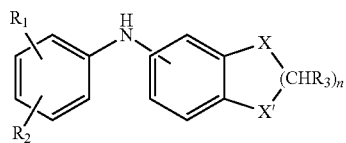

Formula I wherein

R$_1$ and R$_2$ are each independently selected from the group consisting of hydrogen, alkyl from 1 to 20 carbon atoms, —OR, —SR and —NRR', where R and R' are independently hydrogen or alkyl from 1 to 6 carbon atoms, or R$_1$ and R$_2$ when adjacent to each other together form a 5 to 6 membered alicyclic or aromatic ring which may be optionally substituted with 1 or 2 alkyl groups each having from 1 to 20 carbon atoms;

each R$_3$ is hydrogen or alkyl from 1 to 6 carbon atoms,

X and X' are independently selected from —CHR$_4$—, oxygen, sulfur or NR$_5$, wherein R$_4$ and R$_5$ are independently hydrogen or alkyl from 1 to 6 carbon atoms, with the proviso that at least one of X or X' is a heteroatom positioned ortho or para to the bridging nitrogen atom, and when X or X' are nitrogen then R$_1$ or R$_2$ is not hydroxyl; and further provided that when one of X or X' is CHR$_4$— then the other may not be oxygen;

wherein at least one X and X' are oxygen; and n is an integer from 1 to 2.

4. A lubricating oil composition comprising:

a major amount of a base oil of lubricating viscosity from about 40 wt % or more based upon the total lubricating oil composition; and a compound according to formula I:

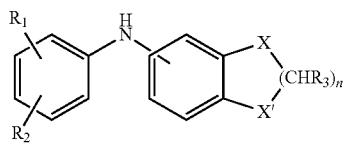

Formula I wherein

R$_1$ and R$_2$ are each independently selected from the group consisting of hydrogen, alkyl from 1 to 20 carbon atoms, —OR, —SR and —NRR', where R and R' are independently hydrogen or alkyl from 1 to 6 carbon atoms, or R$_1$ and R$_2$ when adjacent to each other together form a 5 to 6 membered alicyclic or aromatic ring which may be optionally substituted with 1 or 2 alkyl groups each having from 1 to 20 carbon atoms;

each R$_3$ is hydrogen or alkyl from 1 to 6 carbon atoms,

X and X' are independently selected from —CHR$_4$—, oxygen, sulfur or NR$_5$, wherein R$_4$ and R$_5$ are independently hydrogen or alkyl from 1 to 6 carbon atoms, with the proviso that at least one of X or X' is a heteroatom positioned ortho or para to the bridging nitrogen atom, and when X or X' are nitrogen then R$_1$ or R$_2$ is not hydroxyl; and further provided that when one of X or X' is CHR$_4$— then the other may not be oxygen;

wherein R$_1$ and R$_2$ are adjacent to each other and together form a 5 to 6 membered aromatic ring which may be optionally substituted with 1 or 2 alkyl groups each having from 1 to 20 carbon atoms; and n is an integer from 1 to 2.

5. A lubricating oil composition comprising:

a major amount of a base oil of lubricating viscosity from about 40 wt % or more based upon the total lubricating oil composition; and a compound according to formula I:

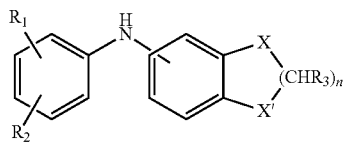

Formula I wherein

R$_1$ and R$_2$ are each independently selected from the group consisting of hydrogen, alkyl from 1 to 20 carbon atoms, —OR, —SR and —NRR', where R and R' are independently hydrogen or alkyl from 1 to 6 carbon atoms, or R$_1$ and R$_2$ when adjacent to each other together form a 5 to 6 membered alicyclic or aromatic ring which may be optionally substituted with 1 or 2 alkyl groups each having from 1 to 20 carbon atoms;

each R$_3$ is hydrogen or alkyl from 1 to 6 carbon atoms,

X and X' are independently selected from —CHR$_4$—, oxygen, sulfur or NR$_5$, wherein R$_4$ and R$_5$ are independently hydrogen or alkyl from 1 to 6 carbon atoms, with the proviso that at least one of X or X' is a heteroatom positioned ortho or para to the bridging nitrogen atom, and when X or X' are nitrogen then R$_1$ or R$_2$ is not hydroxyl; and further provided that when one of X or X' is CHR$_4$— then the other may not be oxygen;

wherein $R_2$ is NRR' where R and R' are alkyl from 1 to 6; and n is an integer from 1 to 2.

6. A lubricating oil composition comprising:

a major amount of a base oil of lubricating viscosity from about 40 wt % or more based upon the total lubricating oil composition; and a compound according to formula I:

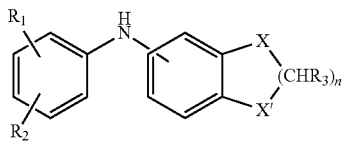

Formula I wherein $R_1$ and $R_2$ are each independently selected from the group consisting of hydrogen, alkyl from 1 to 20 carbon atoms, —OR, —SR and —NRR', where R and R' are independently hydrogen or alkyl from 1 to 6 carbon atoms, or $R_1$ and $R_2$ when adjacent to each other together form a 5 to 6 membered alicyclic or aromatic ring which may be optionally substituted with 1 or 2 alkyl groups each having from 1 to 20 carbon atoms;

each $R_3$ is hydrogen or alkyl from 1 to 6 carbon atoms,

X and X' are independently selected from —$CHR_4$—, oxygen, sulfur or $NR_5$, wherein $R_4$ and $R_5$ are independently hydrogen or alkyl from 1 to 6 carbon atoms, with the proviso that at least one of X or X' is a heteroatom positioned ortho or para to the bridging nitrogen atom, and when X or X' are nitrogen then $R_1$ or $R_2$ is not hydroxyl; and further provided that when one of X or X' is $CHR_4$— then the other may not be oxygen;

wherein X and X' are both selected from $NR_5$, wherein each $R_5$ is independently hydrogen or alkyl from 1 to 6 carbon atoms; and n is an integer from 1 to 2.

7. A lubricating oil composition comprising:

a major amount of a base oil of lubricating viscosity from about 40 wt % or more based upon the total lubricating oil composition; and a compound according to formula I:

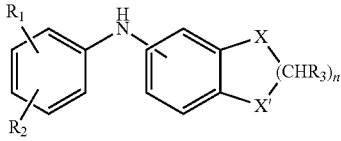

Formula I wherein $R_1$ and $R_2$ are each independently selected from the group consisting of hydrogen, alkyl from 1 to 20 carbon atoms, —OR, —SR and —NRR', where R and R' are independently hydrogen or alkyl from 1 to 6 carbon atoms, or $R_1$ and $R_2$ when adjacent to each other together form a 5 to 6 membered alicyclic or aromatic ring which may be optionally substituted with 1 or 2 alkyl groups each having from 1 to 20 carbon atoms;

each $R_3$ is hydrogen or alkyl from 1 to 6 carbon atoms,

X and X' are independently selected from —$CHR_4$—, oxygen, sulfur or $NR_5$, wherein $R_4$ and $R_5$ are independently hydrogen or alkyl from 1 to 6 carbon atoms, with the proviso that at least one of X or X' is a heteroatom positioned ortho or para to the bridging nitrogen atom, and when X or X' are nitrogen then $R_1$ or $R_2$ is not hydroxyl; and further provided that when one of X or X' is $CHR_4$— then the other may not be oxygen;

wherein at least one X and X' is oxygen; and n is an integer from 1 to 2.

* * * * *